United States Patent [19]

Johnson et al.

[11] Patent Number: 5,239,121
[45] Date of Patent: Aug. 24, 1993

[54] PROCESS FOR THE PREPARATION OF 2-ARYL-1,3-PROPANEDIOLS

[75] Inventors: Francis Johnson, Setauket, N.Y.; Richard Miller, Woodstown, N.J.

[73] Assignee: Ganes Chemicals Inc., Carlstadt, N.J.

[21] Appl. No.: 945,854

[22] Filed: Sep. 16, 1992

[51] Int. Cl.$^5$ .......................... C07F 5/02; C07F 5/04
[52] U.S. Cl. .......................... 568/6; 568/1; 568/811
[58] Field of Search .......................... 568/1, 6, 811, 867

[56] References Cited

U.S. PATENT DOCUMENTS

| | | | |
|---|---|---|---|
| 2,390,278 | 12/1945 | Sletzinger et al. | 568/867 |
| 2,716,650 | 8/1955 | Blicke | 569/867 |
| 3,141,047 | 7/1964 | Emrick | 568/867 |
| 3,202,694 | 8/1965 | Kirshenbaum et al. | 568/867 |
| 3,251,888 | 5/1966 | Toland | 568/811 |
| 3,978,140 | 8/1976 | Lane et al. | 568/867 |
| 3,985,795 | 10/1976 | Kollar | 568/867 |
| 4,868,327 | 9/1989 | Stiefel | 568/811 |
| 4,873,378 | 10/1989 | Murphy et al. | 568/867 |
| 4,982,016 | 1/1991 | Choi | 568/814 |
| 5,072,056 | 12/1991 | Stiefel | 568/814 |

FOREIGN PATENT DOCUMENTS 0125032 11/1984 European Pat. Off. ............ 568/1
0084340 6/1980 Japan ............ 568/1

OTHER PUBLICATIONS

Boeseken, J. et al., "On The Composition Of Acid Boric Acid-Diol Compounds", *Journal of Physical Chemistry*, vol. 35, 1477-1489 (1931).

Bankowska et al., "Transmission of Substituent Effects in the α-Phenylacrylic Acid System", 8 Polish Journal of Chemistry Nov. 1981.

Schwenker et al., "Notiz Über eine neue, allgemein anwendbare Tropasäureestersynthese", Ber., 99, 2407 (1966).

Fujimura et al., "Steroselective Construction of Quaternary Carbons by the Reaction of Aldehydes with Allylic Chromium Reagents Prepared from 1,3-Diene Monoepoxides and $CrCl_2$", J. Org. Chem. 1990, 55, 1705-1706.

*Primary Examiner*—Werren B. Lone
*Attorney, Agent, or Firm*—Watov & Kipnes

[57] ABSTRACT

Process for the production of 2-aryl-1,3-propanediols from a tropate ester and novel intermediate compounds produced thereby.

16 Claims, No Drawings

PROCESS FOR THE PREPARATION OF 2-ARYL-1,3-PROPANEDIOLS

FIELD OF THE INVENTION

The present invention is directed to the preparation of 2-aryl-1,3-propanediols from esters of aryl acetic acids in which the esters are reduced in a simple, inexpensive manner in relatively high yields and to novel intermediate compounds obtained thereby.

BACKGROUND OF THE INVENTION

Glycols, particularly aryl substituted 1,3-propanediols are valuable chemical compounds useful as intermediates for the preparation of a variety of pharmaceutical compounds.

Much attention has been directed to the preparation of these propanediols in commercial quantities. The ideal process utilizes inexpensive reactants, operates under mild conditions and obtains the desired product in high yields.

A number of processes have been disclosed for making 1,3-propanediols on a commercial scale. For example, Frank J. Stiefel, U.S. Pat. Nos. 4,868,327 and 5,072,056, disclose a method of preparing 2-phenyl-1,3-propanediol by forming a benzaldehyde oxime and oxidizing the oxime to produce nitromethylbenzene. This compound is allowed to react with formaldehyde to form 2-nitro-2-phenyl-1,3-propanediol which is then hydrogenated in the presence of a palladium catalyst to produce the diol.

Mark A. Murphy et al., U.S. Pat. No. 4,873,378 discloses the hydrocarbonylation reaction of an epoxide using rhodium as a catalyst.

Young M. Choi, U.S. Pat. No. 4,982,016 discloses a process in which diethyl phenylmalonate is reduced with a metal hydride complex in solution with a heterocyclic ether such as tetrahydrofuran.

While some of these processes have been commercialized, the preparation of 2-aryl-1,3-propanediols remains expensive to manufacture on a commercial scale.

It would therefore be of significant benefit particularly for the production of pharmaceutical compounds from 2-aryl-1,3-propanediols to provide a process for making the diols using inexpensive starting materials under mild process conditions and the minimum process steps to obtain the desired product at high yields.

SUMMARY OF THE INVENTION

The present invention is generally directed to the preparation of 2-aryl-1,3-propanediols from esters of aryl acetic acids and to novel intermediate compounds obtained thereby. The process comprises reacting a compound of the Formula (I):

$$ArCH_2COOR \tag{I}$$

wherein Ar is a substituted or unsubstituted aryl group, and R is selected from the group consisting of an alkyl group having 1-5 carbon atoms, an aralkyl group and an aryl group with formaldehyde to yield a compound of the Formula (II):

$$ArCH(CH_2OH)COOR \tag{II}$$

The resulting compound is reduced in the presence of a metal borohydride, preferably an alkali metal or alkaline earth metal borohydride to produce a novel intermediate compound having the Formula (III):

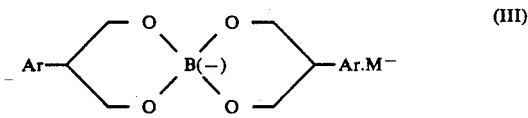

wherein $M^+$ is a metal cation, preferably an alkali or alkaline earth metal cation.

The compound of Formula (III) is then reacted with an acid to remove the cation to yield a compound of the Formula (IV):

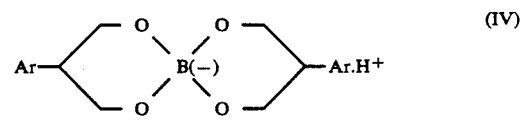

Thereafter, the compound of Formula (IV) is reacted with a base in a hydroxylic solvent, preferably an aqueous solution of an alkali metal carbonate or sodium hydroxide in a lower alkanol such as methanol to produce the desired 2-aryl-1,3-propanediol.

DETAILED DESCRIPTION OF THE INVENTION

The compounds which may be produced in accordance with the present invention comprise 2-aryl-1,3-propanediols. The aryl group includes phenyl, naphthyl, biphenylyl, thienyl and the like. The substituents of the substituted aryl group include halogen (e.g. chlorine), alkoxy having 1-5 carbon atoms, hydroxy, alkyl having 1-5 carbon atoms, amino, nitro, carboxy, acyl, aryloxy, dialkylamino, diarylamino and the like. 2-Phenyl-1,3-propanediol is the preferred and most desirable final product.

The ester of Formula (II) $ArCH(CH_2OH)COOR$ has an R group which may be selected from, for example, lower alkyl having 1-5 carbon atoms, aryl and aralkyl. The preferred lower alkyl groups are methyl and ethyl. The preferred aryl group is phenyl and the preferred substituted aryl groups are benzyl and phenethyl. o-Tolyl, p-tolyl and p-ethylphenyl are the preferred aralkyl groups.

The compound of Formula (I) is allowed to react with formaldehyde in a solvent in the presence of a base. The base may be any alkaline substance and includes, for example, alkali metal hydroxides, carbonates and bicarbonates, alkaline earth metal oxides and hydroxides, and quaternary ammonium compounds such as quaternary ammonium hydroxides, carbonates and bicarbonates. Among the bases which are preferably used are sodium hydroxide, sodium carbonate, sodium bicarbonate, calcium hydroxide, barium hydroxide, magnesium hydroxide and tetrabutylammonium hydroxide. The most preferred bases are sodium and potassium bicarbonate.

The reaction is conducted in an organic solvent including protic and aprotic solvents. Aprotic solvents are preferred because they generally produce higher yields. The preferred solvents include dimethylsulfoxide, N,N-dimethylformamide, N,N-dimethylacetamide and N-methylpyrrolidone.

The resulting ester of Formula (II) may then be reduced either in solution with a borohydride compound or first isolated from the solution such as by fractional distillation. If the latter procedure is used, it is desirable first to neutralize the base that was used as a catalyst by adding a neutralizing amount of an acid including organic acids such as acetic acid, oxalic acid or tartaric acid, or mineral acids, such as hydrochloric acid or sulfuric acid. Neutralization of the base is a preferred step to prevent conversion of the product to acrylic esters by dehydration. The neutralization step therefore obtains higher yields of the desired product of the reaction. This step of the reaction may be conducted at a temperature in the range of from 0° to 100° C., preferably from 20° to 60° C.

The ester of Formula (II) is then reduced with a borohydride compound, preferably selected from sodium, potassium, lithium, calcium, magnesium, lithium-aluminum and quaternary ammonium borohydrides. Sodium borohydride is the most preferred compound. The amount of the borohydride compound is typically in the range of from 0.5 to 1.5 moles/mole of the ester, preferably about 1.0 mole/mole of the ester.

The borohydride compound may be made mildly basic, typically in a pH range of from at least 7.0, preferably 7.0 to 8.5. If necessary, any base which can raise the pH to the desired range may be added to the reaction.

The reduction reaction is carried out in the presence of a solvent. The amount of the solvent is preferably sufficient to form a stirrable mixture although excess solvent may be used without adversely affecting the reaction.

The type of solvent which may be used is unlimited providing the borohydride compound is at least partially soluble in the solvent or one of the solvents if a biphasic system is used. Examples of such solvents include protic and aprotic solvents such as water, lower alkanols (such as ethanol), tetrahydrofuran, dimethylsulfoxide, N,N-dimethylformamide, N,N-dimethylacetamide, N-methylpyrrolidone, 1,2-dimethoxyethane and the like. In addition, a biphasic system employing both aqueous and organic phases may be used. In the latter case, the organic phase may be the tropic ester itself if it is a liquid.

If a protic solvent is used, the reduction reaction is preferably conducted at a temperature of from −10° C. to 30° C. A higher temperature range of from 10° C. to 160° C., preferably about 80° C. is used if an aprotic solvent is selected.

Use of an aprotic solvent is preferably accompanied by an anhydrous metal halide catalyst to improve yield. Such catalysts include, for example, aluminum chloride, titanium chloride, stannic chloride, zinc chloride, boron fluoride, magnesium chloride, calcium chloride and the like. The amount of the metal halide used is preferably that which will provide an anion equivalent (e.g. chloride or fluoride) content equal to the molar quantity of the borohydride compound.

If a biphasic system, which includes an aqueous phase, is selected, it is desirable to use a phase-transfer catalyst. Suitable phase-transfer catalysts are well known and include tetrabutylammonium hydroxide, tetrabutylammonium chloride, tetrapropylammonium chloride, methyl tricaprylammonium chloride (Aliquat 336 ®) and the like.

If the anhydrous metal halide catalyst is used in the reduction step, the M+ cation in Formula (III) becomes the metal cation of the selected metal halide catalyst. This embodiment improves the yield of the compound of Formula (III). The desired diol is obtained by reacting the compound of Formula (III) first with an acid and then with a base. The acids may be selected from organic acids such as acetic acid, citric acid, tartaric acid, oxalic acid and the like and/or mineral acids such as hydrochloric acid, sulfuric acid and the like.

If the anhydrous metal halide is not used, the M+ cation of the compound of Formula (III) is the metal cation of the selected borohydride compound. Also in this case, treating the compound of Formula (III) with an acid produces the compound of Formula (IV).

The resulting compound of Formula (IV) is then decomposed by reaction with a base in a hydroxylic solvent such as an aqueous solution of an alkali metal carbonate such as sodium carbonate, potassium carbonate and the like. Sodium carbonate is particularly preferred. Alternatively, the reaction may be conducted in sodium hydroxide in a lower alkanol such as methanol.

EXAMPLE 1

Preparation Of Methyl Tropate

A three necked one-liter flask equipped with a drying tube, a thermometer and a stopper was flame-dried, cooled and then charged with sodium bicarbonate (2.1 g; 0.025 mole), paraformaldehyde (34.74 g; 1.1 mole) and 300 mL of dimethylsulfoxide (DMSO). The air in the flask was purged with dry nitrogen and methyl phenylacetate (150:18 g; 1 mole) was added in one portion. Residual ester was washed into the flask using dry DMSO (5 mL). The slurry was then stirred magnetically (initial temperature 22°–23° C.) and the temperature rose slowly over one hour to 33° C. The temperature remained at about 32°–33° C. for 1.5 hrs. at which time the reaction liquid was almost a clear solution. The temperature was then raised to 45°–46° C. over 30 min. and kept at this temperature for 12 hrs. The solution was then allowed to cool and left at room temperature for 9 hrs. The reaction mixture was clear and essentially colorless with only a small amount of a white solid appearing at the bottom of the flask. NMR analysis of the solution indicated approximately an 80% yield of methyl tropate.

EXAMPLE 2

Preparation Of 2-Phenyl-1,3-Propanediol

A four-necked 2-liter flask was flame-dried and equipped with a thermometer, an overhead mechanical stirrer, a nitrogen inlet and a drying tube. After cooling to room temperature, a slow flow of nitrogen was commenced and there was added to the flask, fresh sodium borohydride (23.6 g; 0.625 mole) and 1,2-dimethoxyethane (DME;600 mL). The mixture was cooled to 5° C. with stirring and the solution of methyl tropate, prepared as described in Example 1, was added slowly over 25 min. with stirring. A slight exotherm caused the temperature to rise initially, but the temperature was controlled to no higher than 15° C. by means of an ice-water bath.

After adding 50% of the DMSO solution of methyl tropate, the reaction solution became a very thick slurry, but was easily stirrable by the end of the addition. With the solution at 13° C., anhydrous magnesium chloride (8 g; 0.084 mole) was added in one portion. The flask was immediately equipped with a reflux condenser having a drying tube and was then partially immersed in a cold water bath (temp. 25°–27° C.). Over a period of 30 min., the temperature of the reaction mixture rose spontaneously to 68° C. while the bath temperature rose to 35° C. and slight refluxing occurred (due to the methanol produced in the reaction). The mixture was then cooled to 26° C. over 30 mins. by adding ice to the water bath. The remainder of the magnesium chloride (22 g; 0.231 mole; total MgCl$_2$ added = 30 g = 0.315 mole) was then added in one portion with vigorous stirring. No further heat was generated during this addition.

The nitrogen flow was discontinued and the temperature of the contents of the flask (still in the form of a slurry) was raised over 40 min. to reflux (96° C.) and heating was continued for 7 hrs. The thin white slurry was allowed to cool to room temperature then filtered. The white filter cake was washed with a small amount of DME (50 mL) and the combined colorless filtrates were subjected to distillation at the water pump, to remove methanol and dimethoxyethane (total distillate 600 mL) over the temperature range of 66°-80° C.

Dimethylsulfoxide (300 mL) was then removed at the vacuum pump up to an internal liquid temperature of 112° C. (0.3 mm Hg press.). Thereafter, while the pale-yellow thick oily liquid was still hot (110° C.) there was added methyl isobutyl ketone (MIBK; 200 mL) under vigorous stirring. Complete dissolution took place and the liquid was cooled to 30° C. Hydrochloric acid (5N HCl; 120 mL) was added (the pH of the mixture fell to 0.19) and the mixture was stirred for 30 mins. The lower aqueous phase was then separated and solid sodium chloride (5 g) added. This aqueous solution was extracted with additional MIBK (50 mL). The combined organic phases were then washed with saturated brine (10 mL) and the aqueous phase was separated.

The MIBK solution was then mixed with an aqueous 20% solution of sodium carbonate (30 g in 150 mL solution). The mixture was then stirred for 4 hrs. during which time the pH rose from 8.82 to 9.2. The precipitated solid was removed by filtration and washed with MIBK (50 mL) and this filtrate was used separately to wash the aqueous phase of the main filtrate after separation of the major organic phase. The colorless MIBK extracts (400 mL) were combined and washed sequentially with aqueous citric acid solution (15 mL containing 5.6 g citric acid), saturated brine (10 mL), then dried over MgSO$_4$(15 g).

The solution was filtered and the magnesium sulfate was washed with MIBK (10 mL). The MIBK solvent was removed at the water pump (recovery, 290 mL) and the residual oil (115 g) was dissolved in toluene (150 mL) at 25° C. Five minutes after seeding a copious precipitate of white crystals appeared. When precipitation appeared complete, the thick mass was cooled to 5° C. and allowed to stand for 3 hrs. The crystals were removed by filtration washed with cold toluene (2×25 mL) then dried at 30° C. in vacuo to give 2-phenyl-1,3-propanediol (78.1 gm; 51.3% yield).

The toluene filtrate and washings from the isolation of the diol described above, were evaporated (rotary evaporator) to remove toluene (recovered toluene = 136 mL) and the residual oil (33.3 g) was dissolved in MIBK (70 mL). This solution was mixed with 20% sodium carbonate solution (15 mL) and the pH of the MIBK solution rapidly rose from 4.8 to 9.0. The mixture was stirred vigorously for 3 hrs. at 25° C., during which time the pH rose to 9.3. The precipitated solid was removed by filtration, washed with MIBK (5 mL) and dried. This amounted to 4.4 g and was combined with the sodium borate isolated from the first hydrolysis (total— 60.4 g).

The organic phase of the filtrate was separated, washed with citric acid solution (3 mL of a solution containing 5.8 g citric acid in 15 mL of solution) then brine (5 mL), dried over MgSO$_4$ (6 g) and filtered. Removal of MIBK on a rotary evaporator from this filtrate (125 mL) led to the recovery of MIBK (65 mL) and a residual oil (29.0 g). The latter was dissolved in toluene (20 mL), seeded and allowed to stand at 5° C. for 3 hrs. The precipitated solid was removed by filtration, washed with cold toluene (2×10 mL) to give 2-phenyl-1,3-propanediol as a white solid, which was dried under vacuum at 25° C. Yield: 11 g, 7.2% mp. 52.5-54° C., Total Yield-58.5%.

EXAMPLE 3

Preparation Of Methyl Tropate

A nitrogen purged 500 mL three-neck flask was charged with sodium bicarbonate (1.05 g; 0.013 mole), paraformaldehyde (17.37 g; 0.55 mole) and dimethyl sulfoxide (100 mL). Methyl phenylacetate (75.09 g; 0.5 mole) was added and rinsed in with dimethylsulfoxide (50 mL). The slurry was stirred magnetically and the temperature rose from 22° C. to 34° C. over 40 minutes. The temperature remained at 33°-34° C. for about one hour, after which the temperature was raised to 45°-46° C. and held for 12 hours. The reaction mixture was allowed to cool with stirring for about seven hours. A solution of anhydrous oxalic acid (1.13 g; 0.013 mole) in dimethylsulfoxide (6 mL) was added, and the solvent was distilled at pot temperature 45° C. to 100° C. at 0.05 mm Hg. The distillate (153.6 g) was retained. The pale yellow oily residue of crude methyl tropate (112.82 g) contained a small amount of white solid (sodium hydrogen oxalate).

EXAMPLE 4

Preparation Of Boron Complex

A dry 1-liter three-neck flask equipped with mechanical stirrer, thermometer, nitrogen inlet and a dropping funnel was charged with sodium borohydride (14.5 g: 0.375 mole) and ethanol 2B (300 mL) and cooled to −3° C. in an ice/isopropanol bath. The crude methyl tropate from Example 3 was dissolved in ethanol 2B (50 mL) and charged to the dropping funnel, rinsed with ethanol 2B (15 mL), and added to the stirred, cold sodium borohydride slurry over 1 hour 45 minutes while maintaining the temperature between −3° C. and +2° C. The batch was stirred and cooled in an ice bath for about 10 hours, then agitated overnight while warming to room temperature.

The batch was then cooled to 16° C., and a solution of 36% hydrochloric acid (38 mL) in ethanol 2B (35 mL) was added over a period of one-half hour. The pH at this point was 2-3 (paper) and was adjusted to pH 1 by the addition of 36% hydrochloric acid (2 mL). After stirring for one hour, a filter aid (3 g) was added and the mass was filtered through a bed of filter aid (4 g). The cake was washed with ethanol 2B. The salt was dried at 70° C. in vacuo (21.27 g; theoretical 21.94 g). The filtrate and washes were concentrated in vacuo to 70° C. to remove ethanol and the residual pale yellow oily boron-diol chelate (106.72 g) was dissolved in methyl isobutyl ketone (MIBK).

EXAMPLE 5

Preparation Of 2-Phenyl-1,3-Propanediol

A solution of sodium carbonate (22 g; 0.208 mole) in water (85 mL) was added to the solution produced in Example 4, and the mixture stirred vigorously overnight. The solids were separated by filtration, and the cake was washed with MIBK and the washes were held separately. The cake was dried in vacuo at 80° C. (54.54 g). The lower aqueous phase of the main filtrate was separated (pH 9.5) and extracted with the MIBK wash. The combined MIBK layers were washed with citric acid solution (8 mL of a 5.6 g/15 mL solution) and then with saturated brine (10 mL). The MIBK solution was concentrated to one-half volume in vacuo filtered through a small bed of filter aid, and the MIBK was removed in vacuo at 70° C. The pale yellow oily residue (67.98 g) was dissolved in toluene (80 mL) and seeded. The mass was cooled to 0° C. for 2.5 hours, filtered, and the white crystalline product washed with cold toluene. The crystalline product was dried at 40°–45° C. in vacuo to give 2-phenyl-1,3-propanediol (36.07 g, 47.4%).

The mother liquor and toluene washes were combined and concentrated in vacuo to 70° C. to give a pale yellow oil (29.8 g). The oil was dissolved in MIBK (80 mL) and 20% sodium carbonate solution (20 mL) was added and the mass stirred overnight. The solids were separated by filtration (dry weight 4.4 g) and the MIBK solution was washed with citric acid solution (3 mL of 5.6 g in 15 mL) after separating the aqueous layer. The MIBK solution was washed with saturated brine (8 mL) and dried over $MgSO_4$ (4 g). The $MgSO_4$ was separated by filtration and washed with MIBK. The MIBK was removed in vacuo up to 72° C. to give a pale yellow oily residue (25.57 g). The oil was dissolved in toluene (20 mL) and seeded. The product was aged at 0° C., filtered, washed with cold toluene and dried to give 2-phenyl-1,3-propanediol (7.79 g, 10.24%; total yield 57.64%). The mother liquor and wash were concentrated in vacuo to 70° C. to give a pale yellow oily residue (17.09 g).

EXAMPLE 6

Preparation Of Methyl Tropate

A nitrogen purged 500 mL three-neck flask was charged with sodium bicarbonate (1.05 g; 0.013 mole), paraformaldehyde (17.37 g; 0.55 mole) and dimethyl sulfoxide (100 mL). Methyl phenylacetate (75.09 g; 0.5 mole) was added and rinsed in with dimethylsulfoxide (50 mL). The slurry was stirred magnetically and the temperature rose from 22° C. to 34° C. over 40 minutes. The temperature remained at 33°–35° C. for about one hour, after which the temperature was raised to 45°–46° C. and held for 12 hours. The reaction mixture was allowed to cool with stirring for about seven hours. A solution of tartaric acid (1.88 g) in dimethylsulfoxide (6 mL) was added, and the solvent was distilled at pot temperature 45° C. to 88° C. at 0 25 mm Hg. The distillate (168.11 g) was retained. The pale yellow oily residue (97.79 g) which contained a small amount of white solid(sodium hydrogen tartrate) was filtered, then fractionally distilled to give a main cut (59.1 g) of methyl tropate b.p. 106°–112° C. (0.2 mm. Hg).

EXAMPLE 7

Preparation Of 2-Phenyl 1-3,Propanediol

A 500 mL three-neck flask equipped with a mechanical stirrer, thermometer, nitrogen inlet and a dropping funnel was charged with deionized water (150 mL), sodium borohydride (14.5 g; 0.375 mole) and tetra-n-butylammonium chloride (1.0 g.), and the solution was stirred and cooled to 3° C. in an ice bath.

The methyl tropate produced in accordance with Example 3 was added dropwise to the vigorously stirred solution at 3°–5° C., over a period of 1 hour and 50 minutes. The funnel was rinsed with t-butyl methyl ether (31 mL) and the slurry was stirred in an ice bath for an additional nine hours. The slurry was then stirred overnight while it warmed up to room temperature. The batch was cooled in an ice bath and concentrated hydrochloric acid (42 mL) was added to a pH of 1.0.

Solid sodium carbonate (45 g) was added over a period of about 5 minutes, and the pH increased to 9.5. Methyl isobutyl ketone (MIBK; 100 mL) was added and the mixture was agitated overnight. The solids were separated by filtration and washed with MIBK. The solids were dried in vacuo at 75° C. (58.47 g).

The aqueous layer was separated from the filtrate and extracted twice with the MIBK cake washes. The combined MIBK layers were washed with a citric acid solution (8 mL of 5.6 g in 15 mL of solution) and with a saturated salt solution (10 mL). The MIBK solution was then dried over magnesium sulfate (10 g), filtered, and concentrated in vacuo to 72° C. The residual water white oil (61.18 g) was crystallized from toluene (80 mL) and cooled to 0°–5° C. The crystals were separated by filtration, washed with cold toluene and dried in vacuo at 40° C. to give 2-phenyl-1, 3-propanediol (30.95 g; 40.68%). The mother liquor and toluene wash were concentrated to give a water white oil (28.0 g).

The oil recovered from the product diol was dissolved in MIBK (80 mL) and a sodium carbonate solution (20 mL of 20% solution) was added. The mixture was stirred vigorously overnight. The solids were separated by filtration and washed with MIBK. The MIBK filtrate and wash were combined, washed with a citric acid solution (3 mL of a solution of 5.6 g in 15 mL), with saturated salt solution (5 mL) and dried over magnesium sulfate (3 g). The MIBK solution was filtered and concentrated in vacuo to 70° C. The pale yellow oil (27.32 g) was crystallized from toluene (30 mL) and cooled to 0° C. The crystallized product was separated by filtration and dried in vacuo at 45° C. There was obtained 2-phenyl-1,3-propanediol (8.38 g; 11.01%) for a total yield of 51.7%. The toluene mother liquor was concentrated in vacuo at 70° C. to give a water white oil (17.93 g).

EXAMPLE 8

Preparation Of 2-Phenyl-1,3-Propanediol

A 0.5 L. three-neck flask equipped with a mechanical stirrer, thermometer, nitrogen inlet and a dropping funnel was purged with nitrogen, charged with deionized water (75 mL), tetra-n-butyl-ammonium chloride (0.5 g), and sodium borohydride (9.65 g, 0.25 mole), and cooled to 2°–3° C. in an ice bath. Distilled methyl tropate (45.05 g, 0.235 mole; 94% assay), prepared according to Example 6, was added dropwise over a period of 80 minutes at 2°–3° C. The dropping funnel was rinsed into the batch with t-butyl methyl ether (12.5 mL). The slurry was stirred in an ice bath for an additional nine hours, then allowed to stir overnight while warming to room temperature.

The very heavy slurry was cooled to 10° C., and concentrated hydrochloric acid (23 mL) was added to reach a pH of 1.0. Water was added (10 mL) followed by methyl isobutyl ketone (MIBK, 56 mL). The batch was stirred vigorously and solid sodium carbonate (22.5 g) was slowly added. The temperature rose to 30° C. and the slurry was stirred vigorously for 4.5 hours. The solids were separated by filtration and washed with MIBK. The solids were dried at 60° C. in vacuo (30.34 g).

The aqueous layer was separated from the main filtrate and washed twice with the MIBK previously used to wash the solids. The combined MIBK layers were washed twice with citric acid solution (5 mL; 5.6 g in 15 mL water), and with saturated sodium chloride solution (8 mL). The MIBK solution was dried over magnesium sulfate, filtered and concentrated in vacuo to 70° C. to yield a viscous water white oil (37.27 g). Crystallization of the oil from toluene (52 mL) gave after drying at 40° C. in vacuo 2-phenyl-1,3-propanediol (26.73 g, 74.75%; theoretical yield 35.76 g).

The mother liquor and washes from the product were concentrated in vacuo to 75° C. to give a water-white viscous oil (8.68 g). The oil was dissolved in MIBK (27 mL) and stirred vigorously with 20% sodium carbonate solution (8 mL) for four hours. The precipitated solids were filtered, washed with MIBK, and a small amount of aqueous layer was separated from the MIBK solution. The MIBK solution was washed with citric acid solution (3 mL; 5.6 g/15 mL water), with saturated sodium chloride solution (5 mL), and dried over magnesium sulfate. The filtered solution was concentrated in vacuo to 70° C., and the residue (8.25 g) was crystallized from toluene (10 mL). After filtration and drying, there was obtained 2-phenyl-1,3-propanediol (5.31 g, 14.85%). Total yield: 89.6%

The toluene mother liquor and washes obtained above from the secondary recovery were stripped in vacuo to 72° C. to give a pale yellow viscous oil (2.67 g). The oil was dissolved in MIBK (7 mL) and stirred with 20% sodium carbonate solution (3 mL) for 4 hours. When processed as in the secondary recovery, there was obtained 2-phenyl-1,3-propanediol (0.55 g, 1.54%). Overall yield: 91.1%.

The mother liquor and washes were concentrated in vacuo to give a pale yellow oil (2.09 g).

We claim:

1. A method of producing a compound of the Formula (III):

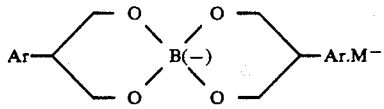

(III)

wherein M+ is a cation selected from the group consisting of sodium, potassium, lithium, calcium, magnesium, lithium-aluminum and quaternary ammonium comprising reacting a compound of the Formula (III):

ArCH(CH₂OH)COOR (II)

wherein Ar is an aryl group selected from the group consisting of phenyl, naphthyl, biphenylyl and thienyl, which may be substituted with a substituent selected from the group consisting of halogen, alkoxy having 1-5 carbon atoms, hydroxy, alkyl having 1-5 carbon atoms, amino, nitro, carboxy, aryloxy, dialkylamino and diarylamino, and R is selected from the group consisting of an alkyl group having 1-5 carbon atoms, an aralkyl group selected from the group consisting of o-tolyl, p-tolyl and p-ethylphenyl and an aryl group selected from the group consisting of phenyl, benzyl and phenethyl with a metal borohydride compound at a pH of at least 7.0 in the presence of at least one solvent.

2. The method of claim 1 wherein the borohydride compound is selected from sodium borohydride, potassium borohydride, lithium borohydride, lithium-aluminum borohydride, calcium borohydride, magnesium borohydride and a quaternary ammonium borohydride.

3. The method of claim 2 wherein the borohydride compound is sodium borohydride.

4. The method of claim wherein the amount of the borohydride compound is from 0.5 to 1.5 moles per mole of the compound of Formula II.

5. The method of claim 1 wherein the solvent is selected from aprotic solvents and protic solvents.

6. The method of claim 5 wherein the solvents are selected from the group consisting of water, lower alkanols, tetrahydrofuran, dimethylsulfoxide, N,N-dimethylformamide, N,N-dimethylacetamide, 1,2-dimethoxyethane and N-methylpyrrolidone.

7. The method of claim 5 wherein the solvent is a protic solvent and the reaction is conducted at a temperature of from −10° C. to 30° C.

8. The method of claim 5 wherein the solvent is an aprotic solvent and the reaction is conducted at a temperature of from 10° C. to 160° C.

9. The method of claim 8 further comprising conducting the reaction in the presence of an anhydrous metal halide catalyst.

10. The method of claim 9 wherein the metal halide catalyst is selected from the group consisting of aluminum chloride, titanium chloride, stannic chloride, zinc chloride, boron fluoride, magnesium chloride and calcium chloride.

11. The method of claim 1 wherein the solvent is a biphasic system comprised of an aqueous phase and an organic phase.

12. The method of claim 11 further comprising conducting the reaction in the presence of a phase-transfer catalyst.

13. A product produced by the process of claim 1.

14. A compound of the Formula (III):

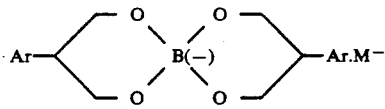

(III)

where Ar is an aryl group selected from the group consisting of phenyl, naphthyl, biphenylyl and thienyl, which may be substituted with a substituent selected from the group consisting of halogen, alkoxy having 1-5 carbon atoms, hydroxy, alkyl having 1-5 carbon atoms, amino, nitro, carboxy, aryloxy, dialkylamino and diarylamino, and M+ is a cation selected from the group consisting of sodium, potassium, lithium, calcium, magnesium, lithium-aluminum and quaternary ammonium.

15. The method of claim 1 wherein Ar is phenyl.

16. The compound of claim 14 where Ar is phenyl.

* * * * *

UNITED STATES PATENT AND TRADEMARK OFFICE
CERTIFICATE OF CORRECTION

Page 1 of 2

PATENT NO. : 5,239,121
DATED : August 24, 1993
INVENTOR(S) : Francis Johnson and Richard Miller It is certified that error appears in the above-indentified patent and that said Letters Patent is hereby corrected as shown below:

Column 2, line 5, delete Formula (III) and substitute therefor:

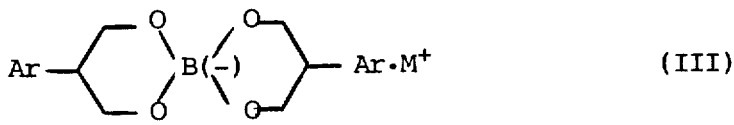 (III)

Column 9, line 55
Claim 1, delete Formula (III) and substitute therefor:

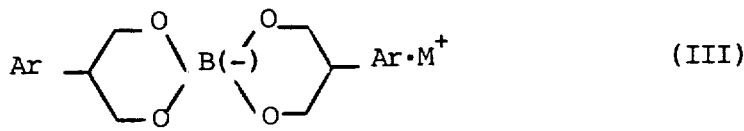 (III)

Column 9,
Claim 1, line 61, change "(III" to --(II)--.

Column 10,
Claim 4, line 18, after "claim" insert --1--.

Claim 14, delete Formula (III) and substitute therefore:

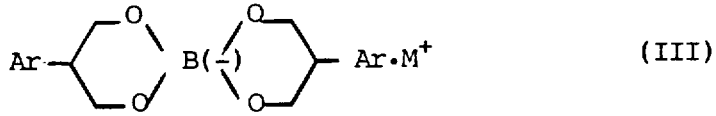 (III)

UNITED STATES PATENT AND TRADEMARK OFFICE
CERTIFICATE OF CORRECTION

PATENT NO. : 5,239,121
DATED : August 24, 1993
INVENTOR(S) : Francis Johnson, et. al.

It is certified that error appears in the above-indentified patent and that said Letters Patent is hereby corrected as shown below:

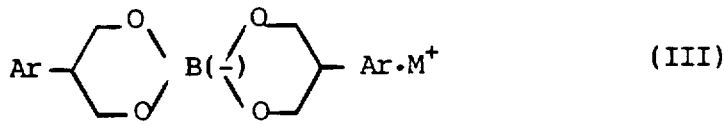  (III)

Signed and Sealed this

Fifteenth Day of March, 1994

Attest:

BRUCE LEHMAN

Attesting Officer    Commissioner of Patents and Trademarks